(12) United States Patent
Oka et al.

(10) Patent No.: US 6,300,507 B2
(45) Date of Patent: Oct. 9, 2001

(54) PROCESS OF MANUFACTURING ETHYLENE OXIDE

(75) Inventors: Yoshihisa Oka, Chigasaki; Kenichi Takematsu, Yokohama, both of (JP)

(73) Assignee: Nippon Shukubai Co Ltd, Osaka (JP)

( * ) Notice: Subject to any disclaimer, the term of this patent is extended or adjusted under 35 U.S.C. 154(b) by 0 days.

(21) Appl. No.: 09/748,283

(22) Filed: Dec. 27, 2000

(30) Foreign Application Priority Data

Dec. 28, 1999 (JP) .................................................. 11-374886

(51) Int. Cl.$^7$ .................................................. C07D 301/10
(52) U.S. Cl. ........................... 549/536; 549/534; 549/537
(58) Field of Search ...................................... 549/534, 536, 549/537

(56) References Cited

U.S. PATENT DOCUMENTS

| 2,279,469 | 4/1942 | Law et al. | 260/348 |
| 2,279,470 | 4/1942 | Law et al. | 260/348 |

*Primary Examiner*—Ba K. Trinh

(57) ABSTRACT

In manufacturing ethylene oxide by catalytic vapor phase oxidation of ethylene, a process comprising adding, as liquid, an organic halide as a reaction inhibitor into the ethylene raw material gas flow is provided. According to this process, ethylene oxide can be manufactured stably and in high selectivity.

13 Claims, 1 Drawing Sheet

PROCESS OF MANUFACTURING ETHYLENE OXIDE

TECHNICAL FIELD TO WHICH THE INVENTION BELONGS

This invention relates to a process of manufacturing ethylene oxide. More detailedly, the invention relates to a process of manufacturing ethylene oxide stably by catalytic vapor phase oxidation reaction.

1. Prior Art

It is widely and industrially carried out to manufacture ethylene oxide by vapor phase oxidation of ethylene in the presence of a silver catalyst. In this process, vapor phase oxidation of ethylene is continuously carried out by contacting an ethylene raw material gas with a silver-containing catalyst loaded into a reactor to partially oxidize the gas, recovering the ethylene oxide in the reaction gas, supplementing the reaction gas containing unreacted ethylene with fresh ethylene, etc. to adjust the gas composition, and then introducing the resulting mixed gas as an ethylene raw material gas into the reactor. In this process, for inhibiting formation of carbon dioxide due to complete combustion of ethylene, it has hitherto been carried out to add an organic halide such as ethylene dichloride (EDC) as a reaction inhibitor into the ethylene raw material gas. This organic halide is added as gas in a slight amount into the ethylene raw material gas.

2. Problems to be Solved by the Invention

However, there has been a problem in the conventional process where the organic halide is added as a gas that the process is insufficient for maintenance of the stability of the oxidation reaction itself and the ethylene oxide selectivity is not satisfyingly high.

Although the ethylene oxide selectivity in today's ethylene oxide manufacturing technology is already in a high level, an increase of the selectivity even if the degree is as small as a few % brings about a large economic effect in view of large production scale of ethylene oxide.

Thus, the object of the invention lies in providing a process of manufacturing ethylene oxide which makes it possible to manufacture ethylene oxide stably and in high selectivity.

3. Means for Solving the Problems

The present inventors have made researches into cause of the above problems, and have found that in the conventional process where a saturated gas formed by bubbling a gas such as ethylene or nitrogen into an organic halide liquid is added to the ethylene raw material gas, it is impossible to add the organic halide always at a constant amount to the ethylene raw material gas, which is a cause of the problems. The reason is that it happens, due to fluctuation of the flow rate and pressure of the ethylene raw material gas to which the organic halide is added, that the organic halide is added in a large amount at a time as a mist. Once the organic halide is added in a large amount at a time, control of the reaction gets very difficult and stable progress of the oxidation reaction gets impossible, for example the reaction being rapidly inhibited or sometimes the reaction being stopped. Moreover, it has also been found that if the addition amount of the organic halide is not constant, problems arise for example that the concentration of the organic halide in the ethylene raw material gas gets ununiform and the ethylene oxide selectivity lowers.

Thus, the present inventors have made vigorous researches into dispersing the organic halide uniformly into the ethylene raw material gas and making the concentration of the organic halide in the ethylene raw material gas substantially uniform, for example, by making the addition amount of the organic halide to the ethylene raw material gas constant.

As addition methods of the organic halide, besides the conventional method where it is added as a gas, the following methods are considered.

(1) Add the organic halide as an aqueous solution to the ethylene raw material gas.

(2) Add the organic halide as a solution in an organic solvent to the ethylene raw material gas.

(3) Add the organic halide itself as liquid to the ethylene raw material gas.

As a result of the present inventors' researches, the following things have been found on these methods (1), (2) and (3).

In the case of the method (1), since the organic halide generally has a low solubility in water and a large specific gravity, dissolution of the organic halide in water gets insufficient and sometimes the reaction gets to be a dangerous state by that the undissolved organic halide enters the reaction system. In the case of the method (2), sometimes, the organic solvent to be used has a bad influence on the oxidation reaction or spoils the quality of the product ethylene oxide.

On the other hand, in the case of the method (3), since, when the organic halide in a liquid state is sent in a pressurized state from its storage tank by a pump and introduced into the ethylene raw material gas, the pressure of the storage tank can, usually, be made lower than the process pressure (the pressure of the ethylene raw material gas), getting to be excessive addition intrinsically does not happen, and it is possible to add a constant amount of the organic halide to the ethylene raw material gas flow in faithful accordance with even fluctuation of the ethylene raw material gas flow.

The invention has been accomplished based on these findings.

Thus, according to the invention, in manufacturing ethylene oxide by catalytic vapor phase oxidation of ethylene in the presence of an organic halide as a reaction inhibitor, a process of manufacturing ethylene oxide comprising adding the organic halide as liquid into the ethylene raw material gas flow is provided.

DESCRIPTION OF THE DRAWINGS

In the attached drawings,

In FIG. 1 and FIG. 2, the meaning of each figure is as follows:

Figure 1:
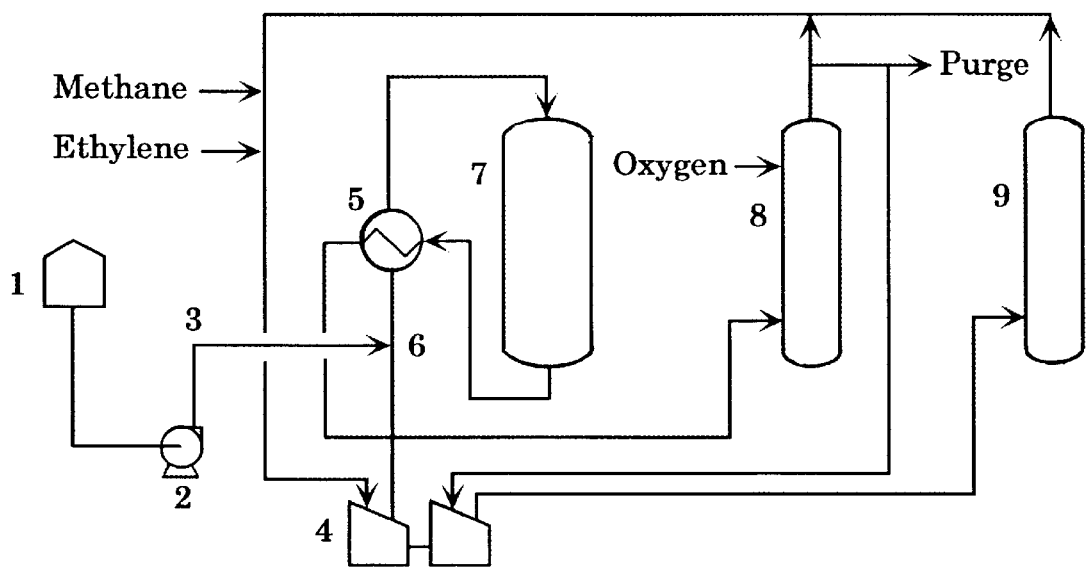
FIG. 1 is a flow sheet showing an embodiment of the invention.

1 Organic halide tank
2 Liquid-sending pump
3 Organic halide feed line
4 Blower
5 Heat exchanger
6 Organic halide addition site
7 Reactor
8 Ethylene oxide-absorbing column
9 Carbon dioxide-absorbing column
10 Organic halide-adding nozzle.

Embodiments of Working of the Invention

An embodiment of the invention is described below according to FIG. 1. An ethylene raw material gas containing ethylene, oxygen, inert gases, etc. is introduced into a shell and tube type reactor 7 via a blower 4 and a heat exchanger 5, and contacted here with a silver-containing catalyst whereby ethylene is partially oxidized into ethylene oxide. The reaction gas is introduced into an ethylene oxide-absorbing column 8 via the heat exchanger 5, and the formed ethylene oxide contained in the reaction gas is absorbed and recovered here. Part of the reaction gas from the ethylene oxide-absorbing column 8 is recycled into the reactor 7, and the rest thereof is, after part thereof being purged, introduced into a carbon dioxide-absorbing column 9 via the blower 4, and after the carbon dioxide being absorbed and separated here, recycled into the reactor 7. The reaction gas thus recycled from the ethylene oxide-absorbing column 8 and the carbon dioxide-absorbing column 9 is, after being supplemented with ethylene, methane, etc. to adjust the gas composition, introduced into the reactor 7 as an ethylene raw material gas, whereby the oxidation reaction is carried out continuously. Usually, the reaction gas is supplemented with oxygen at the ethylene oxide-absorbing column 8.

An organic halide as a reaction inhibitor is transferred from an organic halide tank 1 via an organic halide feed line 3 by a liquid-transferring pump 2, and added as liquid at an organic halide addition site 6. The characteristic of the invention lies in adding the organic halide as liquid into the raw material gas flow.

In the invention, the organic halide can be added into the ethylene raw material gas flow at any site of from the outlet of the blower 4 to the inlet of the reactor 7 in FIG. 1, but it is recommended to add it at a site (e.g., 6) of from the outlet of the blower 4 to the inlet of the heat exchanger 5.

The "ethylene raw material gas" in this specification means a raw material gas introduced into the reactor, namely a mixed gas consisting of ethylene, oxygen, methane, etc. Usually, this ethylene raw material gas is adjusted in its composition by supplementing the reaction gas recycled in the continuous reaction with fresh ethylene, methane, etc.

In the invention, it is desirable to maintain the temperature of the ethylene raw material gas flow at a temperature higher than the dew point of the ethylene raw material gas, preferably at a temperature at least 2° C. higher than the dew point and not more than 150° C. Thereby, the organic halide is almost uniformly vaporized and dispersed into the ethylene raw material gas, and the vapor phase oxidation of ethylene can be carried out stably and complete combustion can effectively be prevented. The reason is not clear, but it is considered that when the temperature of the ethylene raw material gas is equal to or lower than the dew point, moisture in the ethylene raw material gas is present as mist or it is possible that the moisture gets to be mist, and when the organic halide liquid before vaporization collides with this mist, the organic halide liquid is carried away as drain and stable partial oxidation of ethylene is prevented.

In the invention, it is desirable to maintain the mass velocity of the ethylene raw material gas flow at 50 to 2,000 $kg/m^2 \cdot sec$, preferably 100 to 1,000 $kg/m^2 \cdot sec$. Thereby, the organic halide is rapidly vaporized and the concentration of the organic halide in the ethylene raw material gas gets uniform. As a result, the vapor phase oxidation of ethylene can be carried out stably, and the reaction inhibition effect of the organic halide is sufficiently displayed, and the ethylene oxide selectivity is heightened. The "mass velocity" means the mass of the ethylene reaction gas passing through a unit cross section per unit time.

Thus, according to a preferred embodiment of the invention, the organic halide is added as liquid into the ethylene raw material gas flow maintained at a temperature higher than the dew point and at a mass velocity of 50 to 2,000 $kg/m^2 \cdot sec$.

Figure 2:
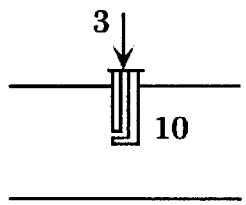
FIG. 2 is a schematic drawing of the longitudinal section of a nozzle used in the invention.

The organic halide is, usually, introduced from a nozzle open to the ethylene raw material gas flow, and, preferably, introduced from a nozzle open against the ethylene raw material gas flow, and, more preferably, introduced from a nozzle open against the upstream direction of the ethylene raw material gas flow. FIG. 2 is a schematic drawing of the longitudinal section of a nozzle wherein an outlet for the organic halide is placed against the upstream direction of the ethylene raw material gas flow.

By thus introducing the organic halide from a nozzle open against the upstream direction of the ethylene raw material gas flow, rapid vaporization and uniform diffusion of the organic halide into the ethylene raw material gas can be accelerated, and the concentration of the organic halide in the ethylene raw material gas can be made further uniform. The aperture of the nozzle is preferably 0.1 to 5 mm. When the aperture is too large, it gets difficult to keep the addition amount of the organic halide constant, and when the aperture is too small, pressure loss gets large and precision processing gets necessary which results in high costs. In order to make the diffusion of the organic halide uniform, it is preferred to place the outlet in the neighborhood of the center of the cross section of the ethylene raw material gas conduit.

As the organic halide in the invention, there can be used, among organic halides generally used as a reaction inhibitor in manufacture of ethylene oxide by vapor phase oxidation of ethylene, any of those which are liquids and vaporize at the time of addition and those which are gases but can be liquefied and added as liquid. As representative examples thereof, there can be mentioned methyl chloride, ethyl chloride, vinyl chloride, ethylene dichloride, etc. Among them, ethylene dichloride is preferably used.

As to the addition amount of the organic halide, there is no particular limitation, and it can appropriately be selected in the range of addition amount generally used on the organic halide (0.01 ppm to some tens ppm (volume)).

There is no particular limitation about the process itself of manufacturing ethylene oxide by catalytic vapor phase oxidation of ethylene, and processes, apparatuses, reaction conditions, etc. generally used for manufacture of ethylene oxide can be adopted.

Effect of the Invention

According to the invention, a constant amount of the organic halide can be added into the ethylene raw material gas. Therefore, the organic halide can be dispersed uniformly into the ethylene raw material gas, and the concentration of the organic halide in the ethylene raw material gas can be made substantially uniform. As a result, the oxidation reaction is stabilized, the reaction inhibition effect of the organic halide is sufficiently displayed, and ethylene oxide selectivity is heightened.

EXAMPLE

The invention is further specifically described below according to an example.

Example 1

A silver-containing catalyst was loaded into the tube side of a shell and tube type reactor, and an ethylene raw material gas consisting of ethylene, oxygen, inert gases, etc. was passed through the catalyst loading layer of the reactor at a pressure of 2.5 MPa and at a temperature of 220 to 240° C. to continuously manufacture ethylene oxide at a production rate of 10 to 12 tons/hour over a period of 11 months. During the continuous manufacture, in order to maintain the concentration of ethylene dichloride (EDC) in the reaction gas at 2.5 ppm (volume), liquid EDC was continuously added into the conduit between the outlet of the blower and the heat exchanger. The addition rate was varied around 200 ml/hour in accordance with the fluctuation of the production amount. The gas temperature at the inlet of the blower was 20 to 33° C., the gas temperature at the outlet of the blower was 36 to 45° C. and the mass velocity of the gas was 350 to 420 kg/m$^2$·sec. The EDC addition nozzle was placed so that the outlet having an aperture of 1 mm could face to the upstream direction of the ethylene raw material gas.

During the continuous running over a period of 11 months, it was confirmed by daily checking the liquid level of the EDC tank that EDC was added at a steady addition rate into the ethylene raw material gas flow. As a result of such an addition method of EDC, it was possible, during the whole running period, to continue the reaction stably without forming any reaction abnormality due to EDC.

What is claimed is:

1. In manufacturing ethylene oxide by catalytic vapor phase oxidation of ethylene in the presence of an organic halide as a reaction inhibitor, a process of manufacturing ethylene oxide comprising adding the organic halide as liquid into the ethylene raw material gas flow.

2. The process according to claim 1 wherein the temperature of the ethylene raw material gas flow is maintained so as to be higher than the dew point.

3. The process according to claim 1 wherein the mass velocity of the ethylene raw material gas flow is maintained at 50 to 2,000 kg/m$^2$·sec.

4. The process according to claim 1, wherein the organic halide is introduced from a nozzle having an opening of 0.1 to 5 mm into the ethylene raw material gas flow.

5. The process according to claim 2 wherein the mass velocity of the ethylene raw material gas flow is maintained at 50 to 2,000 kg/m$^2$·sec.

6. The process according to claim 2 wherein the organic halide is introduced from a nozzle having an opening of 0.1 to 5 mm into the ethylene raw material gas flow.

7. The process according to claim 3 wherein the organic halide is introduced from a nozzle having an opening of 0.1 to 5 mm into the ethylene raw material gas flow.

8. The process according to claim 5 wherein the organic halide is introduced from a nozzle having an opening of 0.1 to 5 mm into the ethylene raw material gas flow.

9. In a process for producing ethylene oxide by catalytically oxidizing ethylene, in an ethylene-containing raw gas feed material, in the presence of an organic halide, as a reaction inhibitor, the improvement comprising introducing liquid organic halide directly into the ethylene-containing raw gas feed material.

10. The improved process according to claim 9, further comprising introducing the liquid organic halide into the raw gas feed material in countercurrent flow to the flow direction of the raw gas feed material.

11. The improved process according to claim 10, which further comprises introducing the liquid organic halide into the raw gas feed material under pressure lower than the pressure of the raw gas feed material.

12. The improved process according to claim 11, which further comprises subjecting the raw gas feed material to which the liquid organic halide has been introduced to heat exchange prior to subjecting the ethylene contained in said raw gas feed material to catalytic oxidation.

13. The improved process according to any one of claims 9–12, which further comprises maintaining the ethylene-containing raw gas feed material at a temperature above the dew point of the raw gas feed material and at a mass velocity of from 50 to 2,000 kg/m$^2$·sec.

* * * * *